US00PP33311P2

(12) United States Plant Patent
Moucheboeuf

(10) Patent No.: US PP33,311 P2
(45) Date of Patent: Aug. 3, 2021

(54) ***DIANTHUS* PLANT NAMED 'WP19 VAL01'**

(50) Latin Name: ***Dianthus* x *allwoodii* hort.**
Varietal Denomination: WP19 VAL01

(71) Applicant: Plant Genetics International, Ltd., Chichester (GB)

(72) Inventor: Laetitia Moucheboeuf, Dawlish (GB)

(73) Assignee: Plant Genetics International, Ltd, Hambrook (GB)

( * ) Notice: Subject to any disclaimer, the term of this patent is extended or adjusted under 35 U.S.C. 154(b) by 0 days.

(21) Appl. No.: 16/911,700

(22) Filed: Jun. 25, 2020

(51) Int. Cl.
*A01H 5/02* (2018.01)
*A01H 6/30* (2018.01)

(52) U.S. Cl.
USPC ..... Plt./275

(58) Field of Classification Search
USPC ..... Plt./275
CPC ... A01H 5/02; A01H 5/00; A01H 6/30; A01H 6/305
See application file for complete search history.

(56) References Cited

PUBLICATIONS

Aris Green Leaf 2019-2020, retrieved on Nov. 23, 2020, retrieved from the Internet at http://www.glplants.com/system/cms/files/files/000/000/952/original/SS-19024-GLP_Dianthus_WEB-SEQ.pdf, pp. 1-16. (Year: 2020).*

Plant Haven International, Int. Promotional *Dianthus* Hello Yellow 2020, retrieved on Nov. 23, 2020, retrieved from the Internet at https://media.planthaven.com/dev/docs/2020/01/Dianthus-PROMOTIONAL%E2%84%A2-Hello-Yellow.pdf, one page. (Year: 2020).*

* cited by examiner

*Primary Examiner* — June Hwu
(74) *Attorney, Agent, or Firm* — Weatherly IP Solutions, LLC; James M. Weatherly

(57) ABSTRACT

A new cultivar of *Dianthus* plant named 'WP19 VAL01' that is characterized by a compact mounding habit, semi-double yellow flowers, blooming from May through October, with a medium, clove-like fragrance, glaucous blue-green foliage, suitable for use as a flowering plant in pots and containers as well as for use as a cut flower and in bouquets, is disclosed.

2 Drawing Sheets

Genus and species: *Dianthus* x *allwoodii* hort.
Variety denomination: 'WP19 VAL01'.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus* x *allwoodii* hort. and will be referred to hereinafter by the cultivar name 'WP19 VAL01'.

'WP19 VAL01' is a complex hybrid plant that is the product of a long-term breeding program conducted in a cultivated area of Dawlish, Devon, United Kingdom. 'WP19 VAL01' was selected in 2016 for its yellow semi-double flowers, medium clove-like fragrance and glaucous blue-green foliage.

'WP19 VAL01' arose and was selected as a seedling which resulted from the controlled pollination of two prior selections of *Dianthus*. The male parent is *Dianthus* code name 'VAL 13.01' (unpatented and unreleased) and the female parent is *Dianthus* code name 'VAL 09.01' (unpatented and unreleased). The male parent and female parent had both grown within the inventor's stock of breeding lines.

Asexual reproduction of 'WP19 VAL01' was first accomplished in 2016 in a cultivated area of Dawlish, United Kingdom using the propagation method of shoot cuttings.

'WP19 VAL01' has been determined to be stable and reproduces true to type in successive generations of asexual propagation.

SUMMARY

The following traits have been repeatedly observed and represent the characteristics of the new *Dianthus* cultivar 'WP19 VAL01'. 'WP19 VAL01' has not been tested under all possible conditions and phenotypic differences may be observed with variations in environmental, climatic and cultural conditions, however, without any variance in genotype.

1. 'WP19 VAL01' exhibits a dense, compact mounding habit.
2. 'WP19 VAL01' bears semi-double yellow flowers.
3. The petals of 'WP19 VAL01' are wavy.
4. 'WP19 VAL01' blooms from May through October.
5. The flowers of 'WP19 VAL01' exhibit a medium clove-like fragrance.
6. 'WP19 VAL01' exhibits glaucous blue-green foliage.
7. At maturity, the height of the foliage mound of 'WP19 VAL01' is 35 cm, and the width is 23 cm.
8. 'WP19 VAL01' is perennial and is hardy at least to minus 15° Centigrade.
9. 'WP19 VAL01' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP19 VAL01' showing colors as true as it is reasonably possible to obtain in colored reproductions of this type. Colors in the photographs may differ from the color values cited in the detailed botanical description, which accurately describe the actual colors of the new variety 'WP19 VAL01'.

Figure 1:
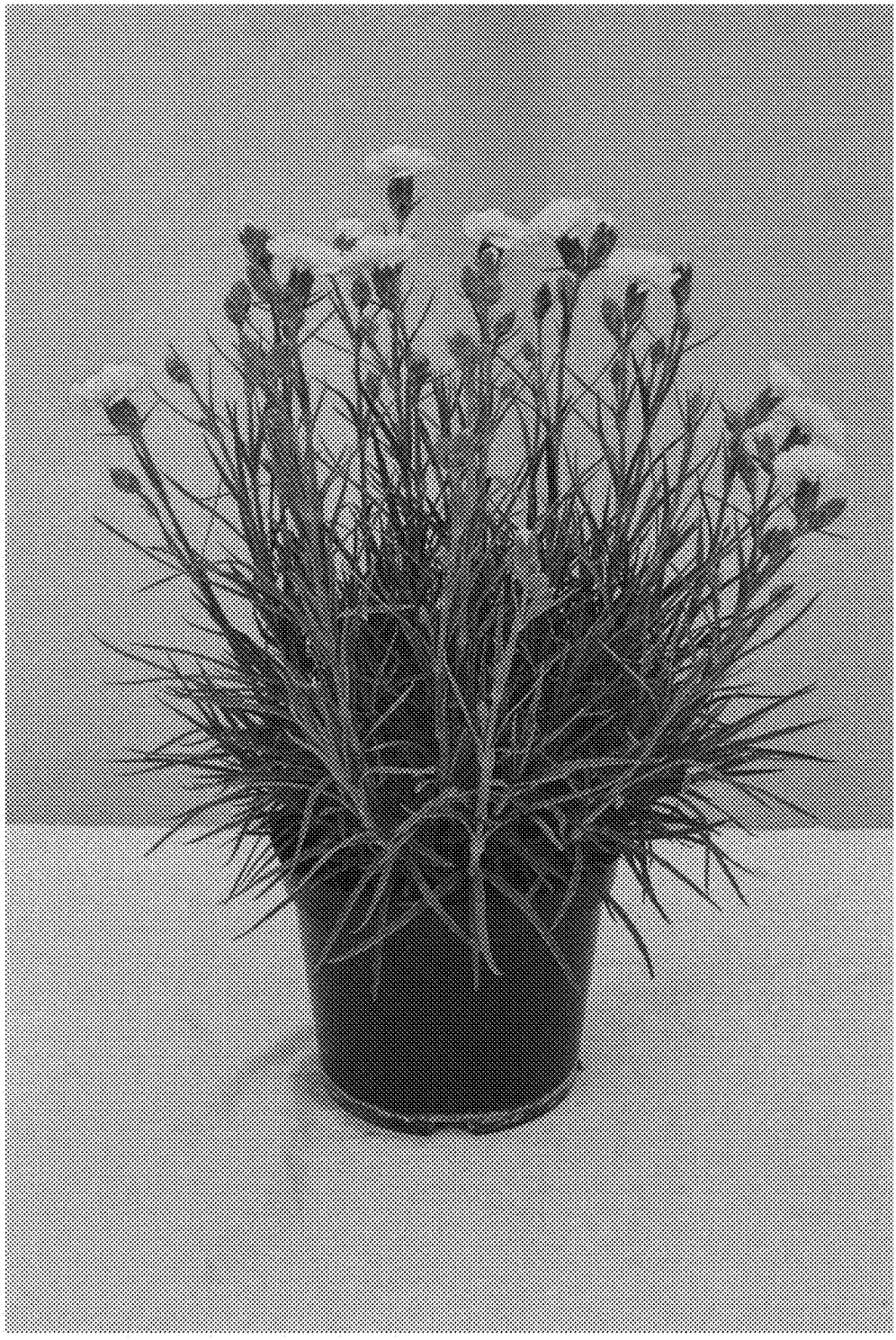
FIG. 1 depicts an entire flowering plant of 'WP19 VAL01'.
Figure 2:
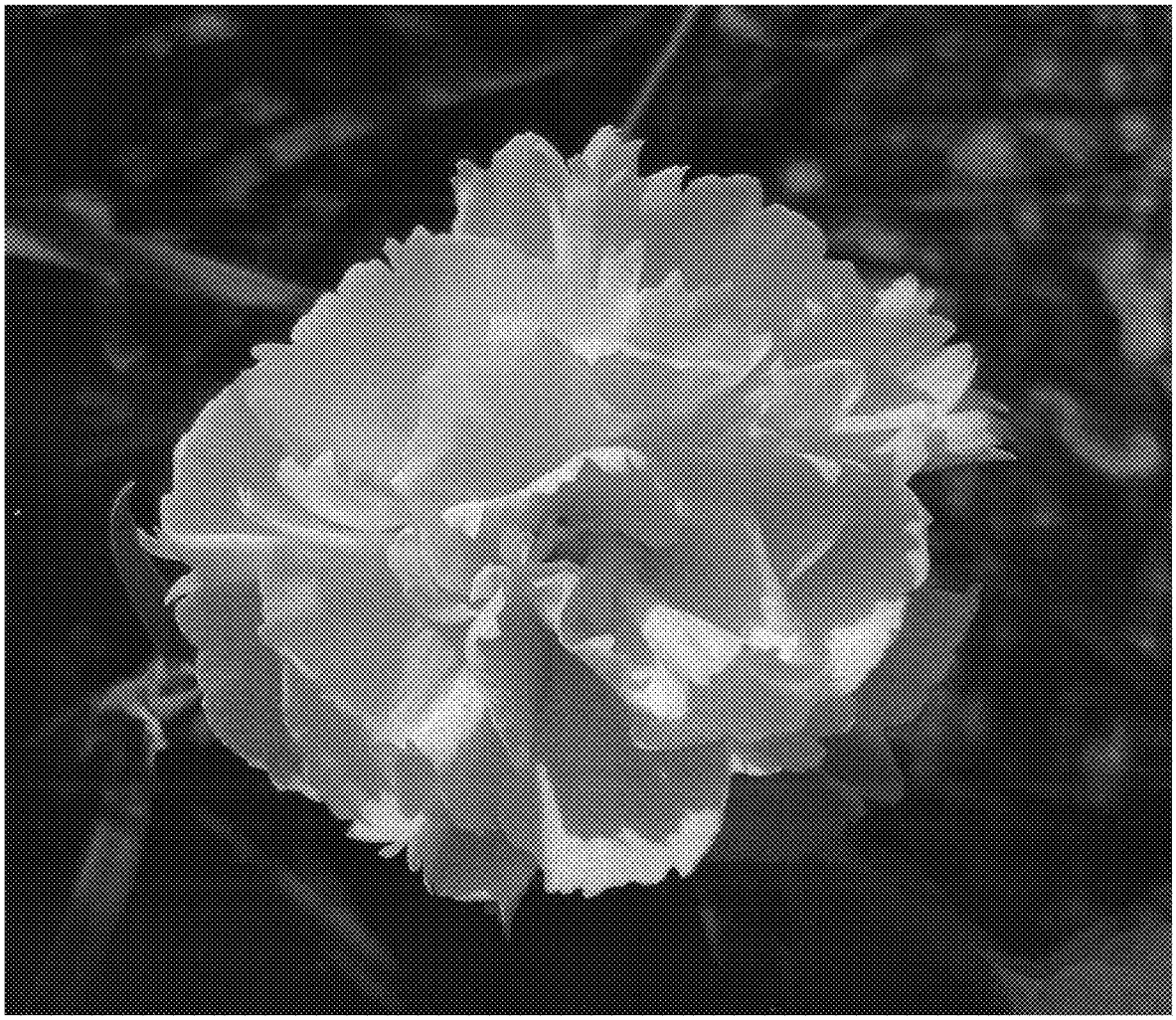
FIG. 2 depicts a close-up view of the flower of 'WP19 VAL01'.

Photographs were taken in May 2020 from a 9 months old plant which has been grown in an unheated greenhouse in Dawlish, United Kingdom in a 3-liter container. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP19 VAL01'. Data was collected from plants grown in 3-liter containers under an unheated glasshouse in Dawlish, United Kingdom. The color determinations are in accordance with the sixth edition (2015) of The Royal Horticultural Society Color Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP19 VAL01'.

*Species*.—X *allwoodii*.

*Common names*.—Hybrid *Dianthus*, Garden Pink.

*Commercial classification*.—Hardy perennial.

*Use*.—Ornamental plant for pots and containers.

Parentage: 'WP19 VAL01' is a hybrid plant that resulted from the controlled cross pollination between two *Dianthus* x *allwoodii* plants.

*Female parent plant*.—'VAL 09.01' experimental *Dianthus* plant (unpatented).

*Male parent plant*.—'VAL 13.01' experimental *Dianthus* plant (unpatented).

Plant description:

*Bloom period*.—May to October.

*Plant habit*.—Dense, compact mounding habit.

*Plant height*.—35 cm in overall height, including flower canopy.

*Plant width*.—23 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished plant in bud and flower in a 3-litre container size from a well-rooted cutting.

Stem:

*Shape*.—Cylindrical, solid.

*Dimensions*.—12 cm in length, 9 mm diameter.

*Surface*.—Glabrous and glaucous.

*Color*.—145B, 145C and 145D (in the sheathing zone).

*Branching*.—Numerous shoots from the axils of the lower leaves.

*Internode length*.—Initially 5 mm to 7 mm increasing to 4 cm-6 cm towards apex.

Leaf:

*Type*.—Evergreen.

*Dimensions*.—10 cm in length, 4 mm in width.

*Color adaxial surface*.—N189B and N189C.

*Color abaxial surface*.—N189B and N189C.

*Shape*.—Linear.

*Curvature*.—Moderately recurved (older basal foliage only).

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Surfaces* (*adaxial and abaxial*).—Strongly glaucous.

*Fragrance*.—Absent.

Flowers:

*Inflorescence*.—Simple cyme.

*Type*.—Semi-double, polypetalous.

*Number*.—3 to 6 per stem.

*Position*.—When fully developed, flowers are borne far above the dense foliage mound.

*Arrangement*.—Fully developed terminal flowers borne singly and in clusters of 2-3 flowers on some lateral branches.

*Dimensions* (*including calyx*).—42 to 44 mm in length and 40 to 44 mm in diameter.

*Shape*.—Circular.

*Lastingness*.—10 days at 20° Celsius on the plant; 8 to 10 days off the plant.

*Fragrance*.—Medium, clove-like.

*Flowering period*.—May to October.

Peduncle:

*Shape*.—Cylindrical, solid.

*Dimensions*.—23 cm to 27 cm in length, 3 to 4 mm in diameter.

*Surface*.—Glabrous, waxy.

*Strength*.—Strong, rigid.

*Color*.—189B.

Bud:

*Shape*.—Cylindrical, without extrusion of styles.

*Color*.—138A to 138B on apical half and 144B to 144C on basal half (below the bracts).

*Anthocyanin*.—Absent.

*Dimensions*.—23 mm in length and 10 mm in width.

Petals:

*Corolla shape, profile*.—Flat convex.

*Corolla dimensions*.—20 to 24 mm in length and 40 to 44 mm in diameter.

*Petal arrangement*.—Persistent, apopetalous and overlapping.

*Margin*.—Crenate-dentate.

*Indentations*.—Medium in number, irregular, up to 2 mm deep.

*Texture*.—Soft.

*Type*.—Semi-double.

*Number of petals*.—15 to 20.

*Dimensions*.—38 mm in length, 25 mm in width.

*Petal shape*.—Fan shape.

*Petal surface*.—Glabrous.

*Petal apex*.—Fan shaped, crenate-dentate.

*Petal base*.—Strap shaped, tapering towards base.

*Color pattern*.—Self-yellow with occasional pink stripes or flecks, 56A.

*Macules*.—Absent.

*Petal color* (*adaxial surface*).—Ground color of blade: 2C and 3C. Color of middle of strap: 4D. Color of base of strap: 145D.

*Petal color* (*abaxial surface*).—Ground color of blade: 1D. Color of middle of strap: 4D. Color of base of strap: 145C.

*Petal color when emerging from the bud occasionally observed*.—23D.

Calyx:

*Dimensions*.—23 mm in length and 12 mm in width.

*Shape*.—Cylindrical and obovate.

*Sepals*.—5, fused up to 5 mm below the apex.

*Sepal dimensions*.—24 mm in length and 7 mm in width.

*Apex*.—Acute.

*Base*.—Truncate.

*Color of sepals, outer surface*.—138A to 138B on apical half and 144B to 144C on basal half (below the bracts).

*Color of sepals, inner surface*.—139D.

*Anthocyanin*.—Absent.

*Splitting*.—Not observed.

Epicalyx:

*Number of bracts*.—1 pair of 2.

*Bracts shape, position*.—Acuminate, adpressed.

*Bracts dimensions*.—12 mm in length and 9 mm in width.

*Bracts color*.—N138A, N138B, N138C and 144B, 144C, 144D are all present.

*Anthocyanin*.—Absent.

*Number of bracteoles*.—1 pair of 2.

*Bracteoles shape, position*.—Acuminate, adpressed

*Bracteoles dimensions*.—14 mm in length and 12 mm in width.

*Bracteoles color*.—N138A, N138B, N138C and 144B, 144C, 144D are all present.

*Bracteoles anthocyanin*.—Absent.

Reproductive organs:

*Stamen number*.—10 to 15 and 0 to 5 petaloid stamen.

*Stamen dimensions*.—25 mm length and 0.5 mm diameter.

*Color of filaments*.—NN155B.

*Anther number*.—1 per stamen, 10 to 15.

*Anther dimensions*.—2 mm length and 1 mm in diameter, often disformed.

*Color of anthers*.—155A (when fresh anthers).

*Anther attachment*.—Dorsifixed.

*Pollen*.—Absent.

*Style number*.—2

*Style shoulder*.—Absent.

*Color of style*.—NN155B.

*Style and stigma dimensions*.—25 mm to 30 mm in length and 1 mm in width.

*Stigma number*.—One on each style.

*Stigma color*.—NN155B.

*Stigma dimensions*.—12 to 15 mm long, fimbriated zone along the top of the style.

*Ovary position*.—Superior.

*Ovary dimensions*.—11 mm in length and 7 mm in diameter.

*Ovary shape*.—Rhombic.

*Ovary surface and texture*.—Smooth and slightly ribbed.

*Ovary color*.—144A at the uppermost surface, becoming paler 149D at the lowest surface.

Seed: Not observed.

Diseases and pests: Susceptible to known *Dianthus* pests and disease but no other susceptibilities to pests or disease are known.

COMPARISON WITH PARENTAL LINE AND KNOWN VARIETY

'WP19 VAL01' is distinguishable from the male parent as follows. The flower color of 'VAL 13.01' is bright orange with white stripes and flowering height is much higher.

'WP19 VAL01' is distinguishable from the female parent as follows. The female parent 'VAL 09.01' bears semi-double salmon flowers with white flecks. The vegetative part of 'VAL 09.01' is also more open than 'WP19 VAL01'.

The variety of *Dianthus* considered to most closely resemble 'WP19 VAL01' is *Dianthus* Plant Named 'Devon Cream' (unpatented). Both 'Devon Cream' and 'WP19 VAL01' are cold-hardy varieties with similar glaucous blue green foliage and with flower colors in the cream-yellow range. In comparison, the flower color of 'Devon Cream' is cream-yellow with pale pink stripes, whereas the flower color of 'WP19 VAL01' is distinctly self-yellow. In addition, whereas the plant habit of 'WP19 VAL01' is tight and compact, the plant habit of 'Devon Cream' is loose and open, and plants of 'Devon Cream' bear much taller flower stems.

I claim:

1. A new and distinct cultivar of *Dianthus* Plant Named 'WP19 VAL01' as described and illustrated herein.

* * * * *